United States Patent [19]
Vale, Jr. et al.

[11] Patent Number: 4,740,500
[45] Date of Patent: Apr. 26, 1988

[54] GNRH ANTAGONISTS VIII

[75] Inventors: Wylie W. Vale, Jr.; Jean E. F. Rivier, both of La Jolla, Calif.

[73] Assignee: The Salk Institute for Biological Studies, San Diego, Calif.

[21] Appl. No.: 946,454

[22] Filed: Dec. 23, 1986

Related U.S. Application Data

[63] Continuation-in-part of Ser. No. 696,699, Jan. 31, 1985, abandoned.

[51] Int. Cl.$^4$ .................. A61K 37/43; C07K 7/20
[52] U.S. Cl. ..................... 514/15; 514/800; 530/313
[58] Field of Search ............... 530/313; 514/15, 800

[56] References Cited

U.S. PATENT DOCUMENTS

| | | | |
|---|---|---|---|
| 4,253,997 | 3/1981 | Sarantakis | 530/313 |
| 4,292,313 | 9/1981 | Vale, Jr. et al. | 514/15 |
| 4,341,767 | 7/1982 | Nestor et al. | 514/15 |
| 4,481,190 | 11/1984 | Nestor et al. | 514/15 |
| 4,504,414 | 3/1985 | Folkers et al. | 530/313 |
| 4,547,370 | 10/1985 | Roeske | 514/15 |
| 4,569,927 | 2/1986 | Rivier et al. | 514/15 |

*Primary Examiner*—Delbert R. Phillips
*Attorney, Agent, or Firm*—Fitch, Even, Tabin & Flannery

[57] ABSTRACT

Peptides which inhibit the secretion of gonadotropins by the pituitary gland and inhibit the release of steroids by the gonads. Administration of an effective amount prevents ovulation of female mammalian eggs and/or the release of steroids by the gonads. The peptides have the structure: Ac-$\beta$-D-NAL-$R_2$-D-3PAL-Ser-Arg-$R_6$-Leu-Arg-Pro-$R_{10}$ wherein $R_2$ is Cl-D-Phe, F-D-Phe, $NO_2$-D-Phe, Br-D-Phe, 3,4$Cl_2$-D-Phe or C$\alpha$Me-Cl-D-Phe; $R_6$ is D-3PAL, D-Trp, For-D-Trp, $NO_2$-D-Trp, (imBzl)D-His, D-Tyr or $\beta$-D-NAL; and $R_{10}$ is Gly-$NH_2$, $NHCH_2CH_3$, $NHNHCONH_2$ or D-Ala-$NH_2$.

20 Claims, No Drawings

GNRH ANTAGONISTS VIII

This invention was made with Government support under Grant Nos. HD-13527 and NO1-HD-2-2807 awarded by the National Institutes of Health. The Government has certain rights in this invention.

This application is a continuation-in-part of our application Ser. No. 696,699 filed Jan. 31, 1985, now abandoned.

The present invention relates to peptides which inhibit the release of gonadotropins by the pituitary gland in mammalians, including humans, and to methods of preventing ovulation and/or inhibiting the release of steroids. More particularly, the present invention is directed to peptides which inhibit gonadal function and the release of the steroidal hormones, estrogens, progestins and androgens.

BACKGROUND OF THE INVENTION

One of the hypothalamic hormones acts as a factor that triggers the release of the gonadotropic hormones, particularly LH, and this hormone is referred to herein as GnRH although it has also been referred to as LH-RH and as LRF. GnRH has been isolated and characterized as a decapeptide having the following structure:

Peptides are compounds which contain two or more amino acids in which the carboxyl group of one acid is linked to the amino group of the other acid. The formula for GnRH, as represented above, is in accordance with conventional representation of peptides where the amino group appears to the left and the carboxyl group to the right. The position of the amino acid residue is identified by numbering the amino acid residues from left to right. In the case of GnRH, the hydroxyl portion of the carboxyl group of glycine has been replaced with an amino group ($NH_2$). The abbreviations for the individual amino acid residues above are conventional and are based on the trivial name of the amino acid, e.g. p-Glu is pyroglutamic acid, His is histidine, Trp is tryptophan, Ser is serine, Tyr is tyrosine, Gly is glycine, Leu is Leucine, Arg is arginine, Pro is proline, Phe is phenylalanine, Ala is alanine, Nle is norleucine, Met is methionine and Nva is norvaline. Except for glycine, amino acids of the peptides of the invention are of the L-configuration unless noted otherwise.

There are reasons for desiring to prevent ovulation in female mammalians, and the administration of GnRH analogs that are antagonistic to the normal function of GnRH have been used to prevent ovulation. For this reason, analogs of GnRH which are antagonistic to GnRH are being investigated for their potential use as a contraceptive or for regulating conception periods. Such antagonists have also been found useful to regulate the secretion of gonadotropins in male mammals and can be employed as male contraceptives. It is desired to provide peptides which are strongly antagonistic to endogenous GnRH and which prevent secretion of LH and the release of steroids by the gonads of mammals.

SUMMARY OF THE INVENTION

The present invention provides peptides which inhibit the release of gonadotropins in mammalians, including humans, and also provides methods for inhibiting the release of steroids by the gonads of male and female mammalians. The improved GnRH analogs are antagonistic to GnRH and have an inhibitory effect on the reproduction processes of mammalians. These analogs may be used to inhibit the production of gonadotropins and sex hormones under various circumstances including precocious puberty, hormone dependent neoplasia, dysmenorrhea and endometriosis.

Generally, in accordance with the present invention, peptides have been synthesized which strongly inhibit the secretion of gonadotropins by the pituitary gland of mammalians, including humans, and/or inhibit the release of steroids by the gonads. These peptides are analogs of GnRH wherein Arg is substituted in the 5-position, D-3PAL is substituted in the 3-position, β-(2-naphthyl)D-alanine is substituted in the 1-position (hereinafter β-D-2NAL), a non-basic D-isomer as generally known in the art or in the form of D-3PAL is substituted in the 6-position and a specific substituent is in the 2-position. The substitution in the 10-position is optional. The 1-position substituent is preferably modified so that its alpha-amino group contains acetyl(Ac) or acrylyl(Acr) which is considered an equivalent thereof. Modified D-Phe is present in the 2-position and provides increased antagonistic activity as a result of the specific modifications present in the benzene ring; its alpha carbon atom may optionally also be methylated. A single substitution for hydrogen is made in the para- or 4-position on the benzene ring, with chloro and fluoro being preferred but nitro and bromo being acceptable. A double substitution in the residue may be made, i.e., one on the alpha carbon atom and one in the benzene ring, e.g., $C^\alpha Me$-4Cl-D-Phe. A non-basic D-isomer residue, preferably D-3PAL, β-D-2NAL, (imBzl)D-His, D-Trp or substituted D-Trp, is present in the 6-position; however, other equivalent hydrophobic, non-basic D-isomers may be present. Leu is preferred in the 7-position, although other equivalent residues of about the same size may be used; however, larger residues are preferably avoided as they may interfere with transport to, recognition of, or activation of the receptor.

Because these peptides are highly potent to inhibit release of LH, they are herein referred to as GnRH antagonists. The peptides inhibit ovulation of female mammals when administered at very low levels at proestrus and are also effective to cause resorption of fertilized eggs if administered shortly after conception. These peptides are also effective for the contraceptive treatment of male mammals. The peptides of the invention are considered to be particularly valuable because of their high potency to inhibit the release of LH and FSH without an accompanying undesirable side effect of also causing the release of histamine which can induce transitory edema of the face and/or extremities.

DETAILED DESCRIPTION OF THE PREFERRED EMBODIMENTS

More specifically, the peptides of the present invention are represented by the following formula:

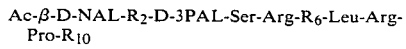

wherein $R_2$ is Cl-D-Phe, F-D-Phe, $NO_2$-D-Phe, Br-D-Phe, $3,4Cl_2$-D-Phe or $C^\alpha Me$-Cl-D-Phe; $R_6$ is D-3PAL, D-Trp, For-D-Trp, $NO_2$-D-Trp, (imBzl)D-His, D-Tyr or β-D-NAL; and $R_{10}$ is Gly-NH$_2$, NHCH$_2$CH$_3$, NHNHCONH$_2$ or D-Ala-NH$_2$.

By β-D-NAL is meant the D-isomer of alanine which is substituted by naphthyl on the β-carbon atom, which may also be designated 3-D-NAL. Preferably β-D-2NAL is employed which means that the β-carbon atom is attached to naphthalene at the 2-position on the ring structure; however, β-D-1NAL is considered an equivalent. By D-3PAL is meant D-alanine which is substituted by pyridyl on the β-carbon atom with the linkage being to the 3-position on the pyridine ring; however D-2PAL and D-4PAL are considered to be equivalents. For substituted D-Trp, either the indole nitrogen is acylated, preferably with formyl (For) or a nitro group is present in either the 5- or preferably the 6-position on the ring. By NML is meant a methyl substitution on the alpha-amino group of Leu.

The peptides of the present invention can be synthesized by classical solution synthesis or by a solid phase technique using a suitable resin, such as a chloromethylated resin, a methylbenzhydrylamine resin(MBHA) or a benzhydrylamine (BHA) resin. The solid phase synthesis is conducted in a manner to stepwise add the amino acids in the chain in the manner set forth in detail in the U.S. Pat. No. 4,211,693. Side-chain protecting groups, as are well known in the art, are preferably added to Ser, Tyr and Arg and may optionally be added to Trp, before these amino acids are coupled to the chain being built upon the resin. The side chain of His is protected by Bzl which is not removed. Such a method provides the fully protected intermediate peptidoresin.

The intermediates of the invention may be represented as: $X^1$-β-D-NAL-$R_2$-D-3PAL-Ser($X^3$)-Arg($X^5$)-$R_6R_6$($X^2$ or $X^4$)-Leu-Arg($X^5$)-Pro-$X^6$ wherein: $X^1$ is an α-amino protecting group of the type known to be useful in the art in the stepwise synthesis of polypeptides. When Ac is present as a substituent on the N-terminal residue, it may be used as the protecting group, if desired. Among the classes of α-amino protecting groups covered by $X^1$ are (1) acyl-type protecting groups, such as formyl (For), trifluoroacetyl, phthalyl, p-toluenesulfonyl (Tos), benzoyl (Bz), benzensulfonyl, o-nitrophenylsulfenyl (Nps), tritylsulfenyl, o-nitrophenoxyacetyl, acrylyl (Acr), chloroacetyl, acetyl (Ac) and γ-chlorobutyryl; (2) aromatic urethan-type protecting groups, e.g., benzyloxycarbonyl (Z) and substituted benzyloxycarbonyl, such as p-chloro-benzyloxycarbonyl, p-nitrobenzyloxycarbonyl, p-bromobenzyloxycarbonyl and p-methoxybenzyloxycarbonyl; (3) aliphatic urethan protecting groups, such as tertbutyloxycarbonyl (Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7) trialkylsilane groups, such as trimethylsilane. The preferred α-amino protecting group is Boc when X is hydrogen.

$X^2$ is hydrogen or a protecting group for the indole nitrogen of Trp, such as formyl or benzyl or for the imidazole group of His, i.e. Bzl; however in many syntheses there is no need to protect Trp.

$X^3$ is hydrogen or a protecting group for the alcoholic hydroxyl group of Ser and is selected from the group consisting of acetyl, benzoyl, tetrahydropyranyl, tert-butyl, trityl, benzyl and 2,6-dichlorobenzyl. Benzyl is preferred.

$X^4$ is hydrogen or a protecting group for the phenolic hydroxyl group of Tyr selected from the group consisting of tetrahydropyranyl, tert-butyl, trityl, benzyl, benzyloxycarbonyl, 4-bromobenzyloxycarbonyl and 2,6-dichlorobenzyl. 2,6-dichlorobenzyl is preferred.

$X^5$ is a protecting group for the nitrogen atoms of Arg and is selected from the group consisting of nitro, Tos, benzyloxycarbonyl, adamantyloxycarbonyl, and Boc; alternatively $X^5$ may be hydrogen, which means there are no protecting groups on the arginine side chain nitrogen atoms. Tos is preferred.

$X^6$ is selected from the group consisting of Gly-O-CH$_2$-[resin support]; O-CH$_2$-[resin support]; D-Ala-O-CH$_2$-[resin support]; Gly-NH-[resin support]; D-Ala-NH-[resin support]; NHNHCONH$_2$ (sometimes referred to as AzaGlyNH$_2$); and OH, ester, amide and hydrazide of either Gly or D-Ala or attached directly to Pro.

The criterion for selecting side chain protecting groups for $X^2$–$X^5$ is that the protecting group should be stable to the reagent under the reaction conditions selected for removing the α-amino protecting group at each step of the synthesis. The protecting group should not be split off under coupling conditions, and the protecting group must be removable upon completion of the synthesis of the desired amino acid sequence under reaction conditions that will not alter the peptide chain.

When the $X^6$ group is Gly-O-CH$_2$-[resin support], D-Ala-O-CH$_2$-[resin support]or O-CH$_2$-[resin support], the ester moiety of one of the many functional groups of the polystyrene resin support is being represented. When the $X^6$ group is Gly-NH-[resin support] or D-Ala-NH-[resin support], an amide bond connects Gly or D-Ala to a resin such as a MBHA resin.

When Ac is not used as the $X^1$ protecting group for the α-amino group of D-NAL, a reaction is preferably carried out with the peptide on the resin (after deblocking the β-amino group while the side-chain groups remain protected), e.g. by reacting with acetic acid in the presence of dicyclohexyl carbodiimide (DCC) or preferably with acetic anhydride or by another suitable reaction as known in the art.

The fully protected peptide can be cleaved from a chloromethylated resin support by ammonolysis, as is well known in the art, to yield the fully protected amide intermediate. Deprotection of the peptide, as well as cleavage of the peptide from a benzhydrylamine resin, can take place at 0° C. with hydrofluoric acid (HF). Anisole or some other suitable scavenger is preferably added to the peptide prior to treatment with HF. After the removal of HF, under vacuum, the cleaved, deprotected peptide is conveniently treated with ether, decanted, taken-up in dilute acetic acid and lyophilized.

Purification of the peptide is effected by ion exchange chromatography on a CMC column, followed by partition chromatography using the elution system: n-butanol; 0.1 N acetic acid (1:1 volume ratio) on a column packed with Sephadex G-25, or by using HPLC, as known in the art.

The invention thus also provides a method for making a peptide or a nontoxic salt thereof, which peptide has the formula: Ac-β-D-NAL-$R_2$-D-3PAL-Ser-Arg-$R_6$-Leu -Arg-Pro-$R_{10}$ wherein $R_2$ is Cl-D-Phe, F-D-Phe, NO$_2$-D-Phe, Br-D-Phe, 3,4Cl$_2$-D-Phe or C Me-Cl-D-Phe; $R_6$ is D-3PAL, D-Trp, For-D-Trp, NO$_2$-D-Trp, (imBzl)D-His, D-Tyr or β-D-NAL; and $R_{10}$ is Gly- NH₂, NHCH₂CH₃, NHNHCONH₂ or D-Ala-NH₂ which method comprises (a) forming an intermediate compound having the formula: X¹-β-D-NAL-R₂-D-3PAL-Ser(X³)-Arg(X⁵) -R₆(X² or X⁴)-Leu-Arg(X⁵)-Pro-X⁶ wherein X¹ is hydrogen or an α-amino protecting group; X² is hydrogen or a protecting group for the indole nitrogen of Trp or for the imidazole nitrogen of His; X³ is hydrogen or a protecting group for the alcoholic hydroxyl group of Ser; X⁴ is hydrogen or a protecting group for the phenolic hydroxyl group of Tyr; X⁵ is hydrogen or a protecting group for the nitrogen atoms of Arg; and X⁶ is selected from the group consisting of Gly-O-CH₂-(resin support), O-CH₂-(resin support), D-Ala-O-CH₂-(resin support), Gly-NH-(resin support), D-Ala-NH-(resin support), Gly-NH₂, NHCH₂CH₃, NHNHCONH₂, amides and esters and hydrazides of Gly or D-Ala; (b) splitting off one or more of the groups X¹ to X⁵ and/or cleaving from any resin support included in X⁶ and, if desired, converting a resulting peptide into a nontoxic salt thereof.

The peptides of the invention are effective at levels of less than 100 micrograms per kilogram of body weight, when administered at about noon on the day of prostrus, to prevent ovulation in female rats. For prolonged suppression of ovulation, it may be necessary to use dosage levels in the range of from about 0.1 to about 2.5 milligrams per kilogram of body weight. These antagonists are also effective as contraceptives when administered to male mammals on a regular basis. Since these compounds will reduce testosterone levels (an undesired consequence in the normal, sexually active male), it may be reasonable to administer replacement dosages of testosterone along with the GnRH antagonist. These antagonists can also be used to regulate the production of gonadotropins and sex steroids for other purposes as indicated hereinbefore.

EXAMPLE

Peptides as indicated in TABLE I having the formula: Ac-R₁-R₂-D-3PAL-Ser-Arg-R₆-R₇Arg-Pro-R₁₀ are prepared by the solid phase procedure referred to above.

TABLE I

| | R₁ | R₂ | R₆ | R₇ | R₁₀ |
|---|---|---|---|---|---|
| 1 | β-D-2NAL | 4Cl—D-Phe | D-Trp | Leu | D-Ala—NH₂ |
| 2 | " | " | D-3PAL | " | " |
| 3 | " | " | β-D-2NAL | " | " |
| 4 | " | " | D-3PAL | " | D-Ala—NH₂(4guaPhe⁵) |
| 5 | dehydroPro | " | β-D-2NAL | 3PAL | D-Ala—NH₂ |
| 6 | " | " | " | Tyr | " |
| 7 | β-D-2NAL | " | D-3PAL | NML | " |
| 8 | " | " | β-D-2NAL | 3PAL | " |
| 9 | " | " | (imBzl)D-His | Leu | " |
| 10 | " | " | 6NO₂—D-Trp | " | " |
| 11 | " | " | D-Tyr | " | " |
| 12 | " | " | (For)D-Trp | " | " |
| 13 | " | 4NO₂—D-Phe | D-Trp | NML | " |
| 14 | " | 4Br—D-Phe | D-Tyr | Nle | NHCH₂CH₃ |
| 15 | Pro | " | (imBzl)D-His | Met | " |
| 16 | dehydroPro | " | D-Trp | Nva | NHNHCONH₂ |
| 17 | " | CᵅMe4Cl—D-Phe | " | " | NHCH₂CH₃ |
| 18 | " | 4F—D-Phe | " | 4F—Phe | D-Ala—NH₂ |
| 19 | " | " | " | NML | NHNHCONH₂ |
| 20 | " | " | D-Trp | Nle | NHCH₂CH₃ |
| 21 | " | " | β-D-2NAL | Trp | Gly—NH₂ |
| 22 | Pro | " | " | Nva | " |
| 23 | β-D-2NAL | 3,4Cl—D-Phe | β-D-1NAL | Tyr | D-Ala—NH₂ |
| 24 | " | " | D-Trp | Met | D-Ala—NH₂ |
| 25 | 4Cl—D-Phe | " | D-Tyr | 3PAL | D-Ala—NH₂(acetate) salt |

For purposes of an example, a representative solid phase synthesis of Peptide No. 1 above, which is referred to as [Ac-β-D-2NAL¹, 4Cl-D-Phe², D-3PAL³, Arg⁵, D-Trp⁶, D-Ala¹⁰]-GnRH is set forth hereinafter. This peptide has the following formula:

Ac-β-D-2NAL-4Cl-D-Phe-D-3PAL-Ser-Arg-D-Trp-Leu-Arg-Pro -D-Ala-NH₂.

A MBHA resin is used, and Boc-protected D-Ala is coupled to the resin over a 2-hour period in CH₂Cl₂ using a 3-fold excess of Boc derivative and DCC as an activating reagent. The alanine residue attaches to the MBHA resin by an amide bond.

Following the coupling of each amino acid residue, washing, deblocking and coupling of the next amino acid residue is carried out in accordance with the following schedule using an automated machine and beginning with about 5 grams of resin:

| STEP | REAGENTS AND OPERATIONS | MIX TIMES MIN. |
|---|---|---|
| 1 | CH₂Cl₂ wash-80 ml. (2 times) | 3 |
| 2 | Methanol(MeOH) wash-30 ml. (2 times) | 3 |
| 3 | CH₂Cl₂ wash-80 ml. (3 times) | 3 |
| 4 | 50 percent TFA plus 5 percent 1,2-ethanedithiol in CH₂CL₂—70 ml. (2 times) | 10 |
| 5 | CH₂Cl₂ wash-80 ml. (2 times) | 3 |
| 6 | TEA 12.5 percent in CH₂Cl₂—70 ml. (2 times) | 5 |
| 7 | MeOH wash-40 ml. (2 times) | 2 |
| 8 | CH₂Cl₂ wash-80 ml. (3 times) | 3 |
| 9 | Boc-amino acid (10 mmoles) in 30 ml. of either | 30–300 |

| STEP | REAGENTS AND OPERATIONS | MIX TIMES MIN. |
|---|---|---|
|  | DMF or CH$_2$Cl$_2$, depending upon the solubility of the particular protected amino acid, (1 time) plus DCC (10 mmoles) in CH$_2$Cl$_2$ |  |
| 10 | MeOH wash-40 ml. (2 times) | 3 |
| 11 | TEA 12.5 percent in CH$_2$Cl$_2$—70 ml. (1 time) | 3 |
| 12 | MeOH wash-30 ml. (2 times) | 3 |
| 13 | CH$_2$Cl$_2$ wash-80 ml. (2 times) | 3 |

After step 13, if the synthesis is performed manually, an aliquot is taken for a ninhydrin test: if the test is negative, go back to step 1 for coupling of the next amino acid; if the test is positive or slightly positive, go back and repeat steps 9 through 13.

The above schedule is used for coupling of each of the amino acids of the peptide of the invention after the first amino acid has been attached. N$^\alpha$Boc protection is used for each of the remaining amino acids throughout the synthesis. N$^\alpha$Boc-$\beta$-D-2NAL is prepared by a method known in the art, e.g. as described in detail in U.S. Pat. No. 4,234,571, issued Nov. 18, 1980. The side chain of Arg is protected with Tos. OBzl is used as a side chain protecting group for the hydroxyl group of Ser, and 2-6 dichlorobenzyl is used as the side chain protecting group for the hydroxyl group of Tyr in synthesizing Peptide No. 6. D-Trp is left unprotected when it is employed. N$^\alpha$Boc-$\beta$-D-2NAL is introduced as the final amino acid. Boc-Arg(Tos) and Boc-D-Trp, which have low solubility in CH$_2$Cl$_2$, are coupled using DMF:CH$_2$Cl$_2$ mixtures.

After deblocking the $\alpha$-amino group at the N-terminal, acetylation is achieved using a large excess of acetic anhydride in dichloromethane. The cleavage of the peptide from the resin and complete deprotection of the side chains takes place very readily at 0° C. with HF. Anisole is added as a scavenger prior to HF treatment. After the removal of HF under vacuum, the resin is extracted with 50% acetic acid, and the washings are lyophilized to provide a crude peptide powder.

Purification of the peptide is then effected by ion exchange chromatography on CMC (Whatman CM 32, using a gradient of 0.05 to 0.3M NH$_4$OAc in 50/50 methanol/water) followed by partition chromatography in a gel filtration column using the elution system: n-Butanol; 0.1 N Acetic acid (1:1 - volume ratio).

The peptide is judged to be homogeneous using reversed-phase high pressure liquid chromatography and an aqueous triethylammonium phosphate solution plus acetonitrile or 0.1% TFA in H$_2$O plus acetonitrile. Amino acid analysis of the resultant, purified peptide is consistent with the formula for the prepared structure, showing substantially integer-values for each amino acid in the chain. The optical rotation is measured on a photoelectric polarimeter as $[\alpha]_D^{22} = -30.3° \pm 1(c=1, 50\%$ acetic acid). Peptide No. 25 is transformed into the acetic acid salt thereof by first desalting using DEAE cellulose and then adding 1 N acetic acid prior to lyophilization. Alternatively treatment can be carried out with CMC and then with ammonium acetate, followed by extensive lyophilization, or by some other suitable method known in the art.

The peptides described hereinabove are tested in vivo to determine their effectiveness to prevent ovulation in female rats. In this test, a specified number of mature female Sprague-Dawley rats, i.e. five or ten, each having a body weight from 225 to 250 grams, is injected with a specified number of micrograms of the peptide in corn oil at about noon on the day of proestrus. Proestrus is the afternoon before estrus (ovulation). A separate female rat group is used as a control to which the peptide is not administered. Each of the control rat females has ovulation at estrus; of the rats treated, none of them ovulates. As a result, the peptide is considered to be significantly effective to prevent ovulation of female rats at a very low dosage, and the peptide is considered to be totally effective at a dose of about ten micrograms. Additional testing is also carried out at lower and higher dosages, with the results being set forth in TABLE II hereinafter. More importantly, testing shows that these antagonists exhibit a very low propensity to cause release of histamine and thus do not produce in vivo edematous effects.

TABLE II

| Peptide No. | $[\alpha]_D^{22}$ | in vivo Dose (μg) | No. Ovulating |
|---|---|---|---|
| 1. | −30.3° ± 1 | 1 | 0/6 |
|  |  | 0.5 | 2/10 |
| 2. | −29.8° ± 1 | 1 | 1/16 |
|  |  | 0.5 | 5/10 |
| 3. |  | 1 | 0/5 |
|  | −34.3° ± 1 | 0.5 | 6/10 |
|  |  | 0.25 | 7/10 |
| 8. |  | 1 | 9/10 |
|  |  | 0.5 | 8/8 |
| 9. | −23.0 ± 1 | 0.5 | 0/6 |
| 10. | −35.0 ± 1 | 0.5 | 0/5 |
| 11. | −29.8 ± 1 | 0.5 | 11/15 |
| 12. | −24.3 ± 1 | 0.5 | 9/20 |

All of the peptides are considered to be effective to prevent ovulation of female mammals at very low dosages. These peptides may be administered in the form of pharmaceutically acceptable, nontoxic salts, such as acid addition salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, maleate, acetate, citrate, benzoate, succinate, alginate, malate, ascorbate, tartrate and the like. If the active ingredient is to be administered in tablet form, the tablet may contain a pharmaceutically-acceptable diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 1 to about 100 micrograms of the peptide per kilogram of the body weight of the host when given intravenously; oral dosages will be higher. Overall, treatment of subjects with these peptides is generally carried out in the same manner as the clinical treatment using other antagonists of GnRH.

These peptides can be administered to mammals intravenously, subcutaneously, intramuscularly, orally, intranasally or intravaginally to achieve fertility inhibition and/or control and also in applications calling for reversible suppression of gonadal activity, such as for the management of precocious puberty or during radiation- or chemo-therapy. They may also be administered in delayed-release formulations. Effective dosages will vary with the form of administration and the particular species of mammal being treated. An example of one typical dosage form is a physiological saline solution containing the peptide which solution is administered to provide a dose in the range of about 0.1 to 2.5 mg/kg of body weight. Oral administration of the peptide may be given in either solid form or liquid form.

Although the invention has been described with regard to its preferred embodiments, it should be understood that changes and modifications as would be obvious to one having the ordinary skill in this art may be made without departing from the scope of the invention which is set forth in the claims which are appended hereto. For example, other substitutions known in the art which do not significantly detract from the effectiveness of the peptides may be employed in the peptides of the invention. For instance, Gly-OCH$_3$, Gly-OCH$_2$CH$_3$, Gly-NHNH$_2$ and Sar-NH$_2$ (Sar=sarcosine) are considered to be equivalents of the residues specified for R$_{10}$. 4gua-Phe is considered to be equivalent to Arg, both of which contain the guanidino group. Instead of the D-isomer substituents set forth for use in the 6-position, suitable hydrophobic D-isomer residues, as set forth in U.S. Pat. No. 4,419,347 (the disclosure of which is incorporated herein by reference) may be used, e.g. 3-(2,4,6-trimethylphenyl)D-Ala, 3-(benzimidazol-2-yl)D-Ala and 3-(4,5,6,7-tetrahydrobenzimidazol-2-yl)D-Ala, or others such as D-Leu, D-Ile, D-Nle, D-Val, D-Ala or D-Ser(OtBu) may also be used.

What is claimed is:

1. A peptide or a nontoxic salt thereof, said peptide having the formula:

Ac-β-D-NAL-R$_2$-D-3PAL-Ser-Arg-R$_6$-Leu-Arg-Pro-R$_{10}$ wherein R$_2$ is Cl-D-Phe, F-D-Phe, NO$_2$-D-Phe, Br-D-Phe, 3,4Cl$_2$-D-Phe or C$^\alpha$Me-Cl-D-Phe; R$_6$ is D-3PAL, D-Trp, For-D-Trp, NO$_2$-D-Trp, (imBzl)D-His, D-Tyr or β-D-NAL; and R$_{10}$ is Gly-NH$_2$, NHCH$_2$CH$_3$, NHNHCONH$_2$ or D-Ala-NH$_2$.

2. A peptide in accordance with claim 1 wherein R$_1$ is β-D-2NAL.

3. A peptide in accordance with claim 2 wherein R$_{10}$ is D-Ala-NH$_2$.

4. A peptide in accordance with claim 3 wherein R$_2$ is 4Cl-D-Phe.

5. A peptide in accordance with claim 4 wherein R$_6$ is β-D-2NAL.

6. A peptide in accordance with claim 4 wherein R$_6$ is D-3PAL.

7. A peptide in accordance with claim 4 wherein R$_6$ is D-Trp.

8. A peptide in accordance with claim 1 wherein R$_6$ is (For)D-Trp.

9. A peptide in accordance with claim 8 wherein R$_2$ is 4Cl-D-Phe.

10. A peptide in accordance with claim 9 wherein R$_{10}$ is D-Ala-NH$_2$.

11. A peptide in accordance with claim 1 wherein R$_6$ is β-D-2NAL.

12. A peptide in accordance with claim 1 wherein R$_6$ is D-Tyr.

13. A peptide in accordance with claim 1 wherein R$_6$ is (imBzl)D-His.

14. A peptide in accordance with claim 1 wherein R$_6$ is 6NO$_2$-D-Trp.

15. A peptide in accordance with claim 1 wherein R$_6$ is (For) D-Trp and R$_{10}$ is D-Ala-NH$_2$.

16. A pharmaceutical composition for regulating the secretion of gonadotropins comprising as an active ingredient an effective amount of a peptide having the formula Ac-β-D-NAL-R$_2$-D-3PAL-Ser-Arg-R$_6$-Leu-Arg-Pro-R$_{10}$ wherein R$_2$ is Cl-D-Phe, F-D-Phe, NO$_2$-D-Phe, Br-D-Phe, 3,4Cl$_2$-D-Phe or C$^\alpha$Me-Cl-D-Phe; R$_6$ is D-3PAL, D-Trp, For-D-Trp, NO$_2$-D-Trp, (imBzl)D-His, D-Tyr or B-D-NAL; and R$_{10}$ is Gly-NH$_2$, NHCH$_2$CH$_3$, NHNHCONH$_2$ or D-Ala-NH$_2$ in association with a major amount of a nontoxic pharmaceutically-acceptable diluent.

17. A method of regulating ovulation and/or the release of steroids by the gonads, which method comprises administering to a mammal an effective amount of peptide or a nontoxic salt thereof, which peptide has the sequence: Ac-β-D-NAL-R$_2$-D-3PAL-Ser-Arg-R$_6$-Leu-Arg-Pro-R$_{10}$ wherein R$_2$ is Cl-D-Phe, F-D-Phe, NO$_2$-D-Phe, Br-D-Phe, 3,4Cl$_2$-D-Phe or C$^\alpha$Me-Cl-D-Phe; R$_6$ is D-3PAL, D-Trp, For-D-Trp, NO$_2$-D-Trp, (imBzl)D-His, D-Tyr or β-D-NAL; and R$_{10}$ is Gly-NH$_2$, NHCH$_2$CH$_3$, NHNHCONH$_2$ or D-Ala-NH$_2$.

18. A method in accordance with claim 17 wherein R$_2$ is 4Cl-D-Phe.

19. A method in accordance with claim 18 wherein R$_6$ is D-3PAL and R$_{10}$ is D-Ala-NH$_2$.

20. A method in accordance with claim 17 wherein R$_6$ is 6NO$_2$-D-Trp and R$_{10}$ is D-Ala-NH$_2$.

* * * * *

UNITED STATES PATENT AND TRADEMARK OFFICE
CERTIFICATE OF CORRECTION

PATENT NO. : 4,740,500
DATED : April 26, 1988
INVENTOR(S) : Wylie W. Vale, Jr. and Jean E. F. Rivier It is certified that error appears in the above-identified patent and that said Letters Patent is hereby corrected as shown below:

Column 3, Line 34, Delete "$R_6$" (second occurrence)

Column 4, Line 40, Change "$\beta$" to --$\alpha$--

Column 5, Lines 48,49, Change "pros-trus" to --proestrus--

Column 10, Line 36, Change "B-D-NAL" to --$\beta$-D-NAL--

Signed and Sealed this

Eighteenth Day of October, 1988

*Attest:*

DONALD J. QUIGG

*Attesting Officer*   *Commissioner of Patents and Trademarks*